United States Patent [19]

Pegnim

[11] 4,207,161

[45] Jun. 10, 1980

[54] DISSOLVED OXYGEN ANALYZER

[75] Inventor: Timothy C. Pegnim, Wilton, Conn.

[73] Assignee: Cambridge Instrument Co., Inc., Ossining, N.Y.

[21] Appl. No.: 969,347

[22] Filed: Dec. 14, 1978

[51] Int. Cl.² ............................................. G01N 27/46
[52] U.S. Cl. .................................................. 204/195 P
[58] Field of Search ............... 204/195 P, 1 P; 324/29; 128/2 E, 635

[56] References Cited

U.S. PATENT DOCUMENTS

| | | | |
|---|---|---|---|
| 3,334,039 | 8/1967 | Vlasak | 204/195 P |
| 3,518,179 | 6/1970 | Bleak et al. | 204/195 P |
| 3,528,904 | 9/1970 | Cliffgard | 204/195 P |
| 3,764,504 | 10/1973 | Arff et al. | 204/195 P |
| 3,795,239 | 3/1974 | Eberhard et al. | 204/195 P X |
| 4,126,531 | 11/1978 | Porter et al. | 204/195 P |
| 4,132,616 | 1/1979 | Tantram et al. | 204/195 P |

*Primary Examiner*—G. L. Kaplan
*Attorney, Agent, or Firm*—Eugene E. Geoffrey, Jr.

[57] ABSTRACT

A dissolved oxygen analyzer which includes a sensor having a lead electrode and lead wire extending therefrom and a silver electrode and silver wire extending therefrom. The electrodes are immersed in an electrolyte and both metals are substantially pure. The silver electrode is positioned in adjoining relationship to an oxygen permeable membrane immersed in a sample water stream being tested. The sensor further includes a pressure equalizing diaphragm in communication with the sample water to maintain uniformity of pressure in the sensor with that of the water and a constant head tank maintains uniform water pressure and a thermistor monitors the water temperature and modifies the output of an amplifier connected to said wires to compensate for temperature changes.

8 Claims, 11 Drawing Figures

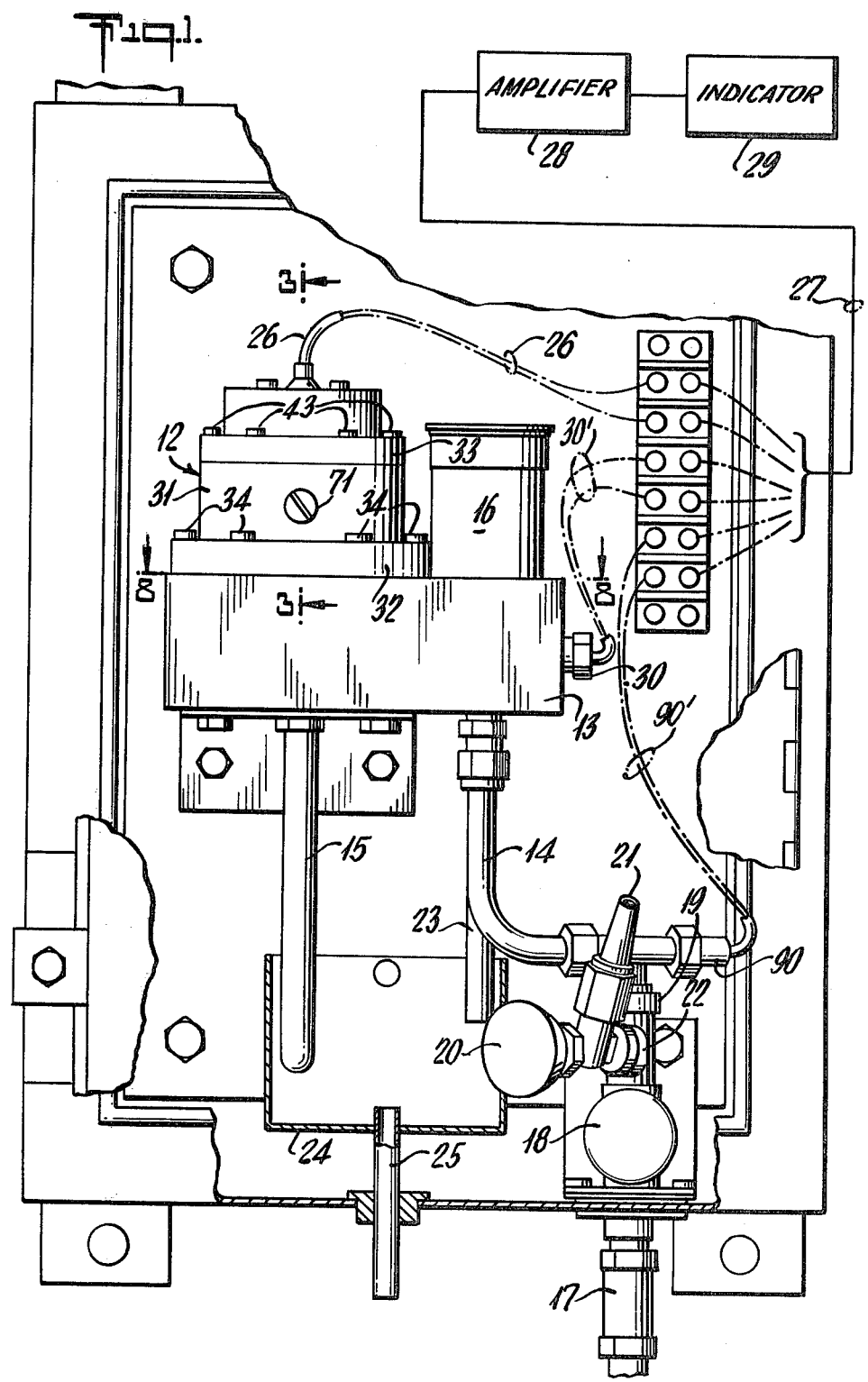

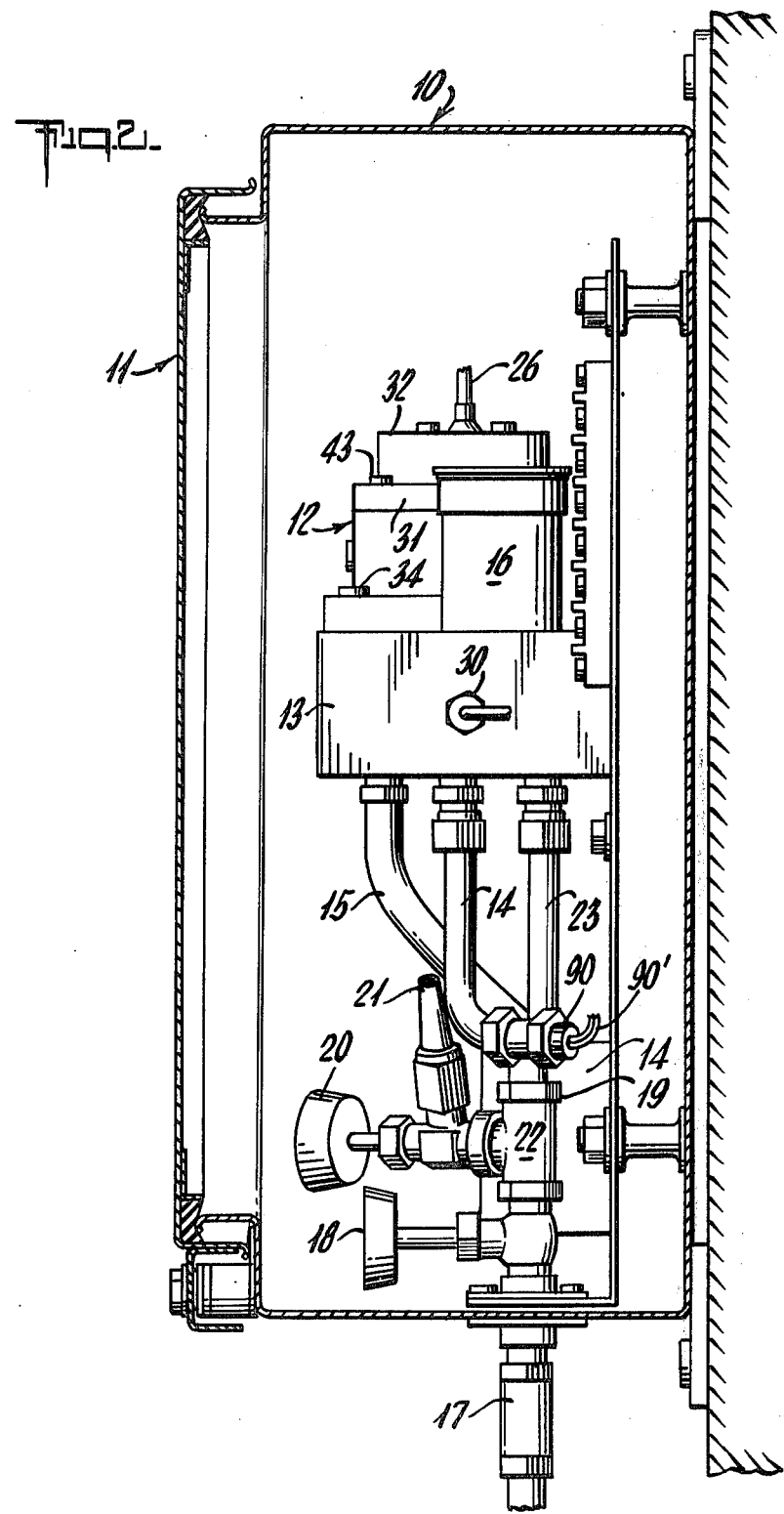

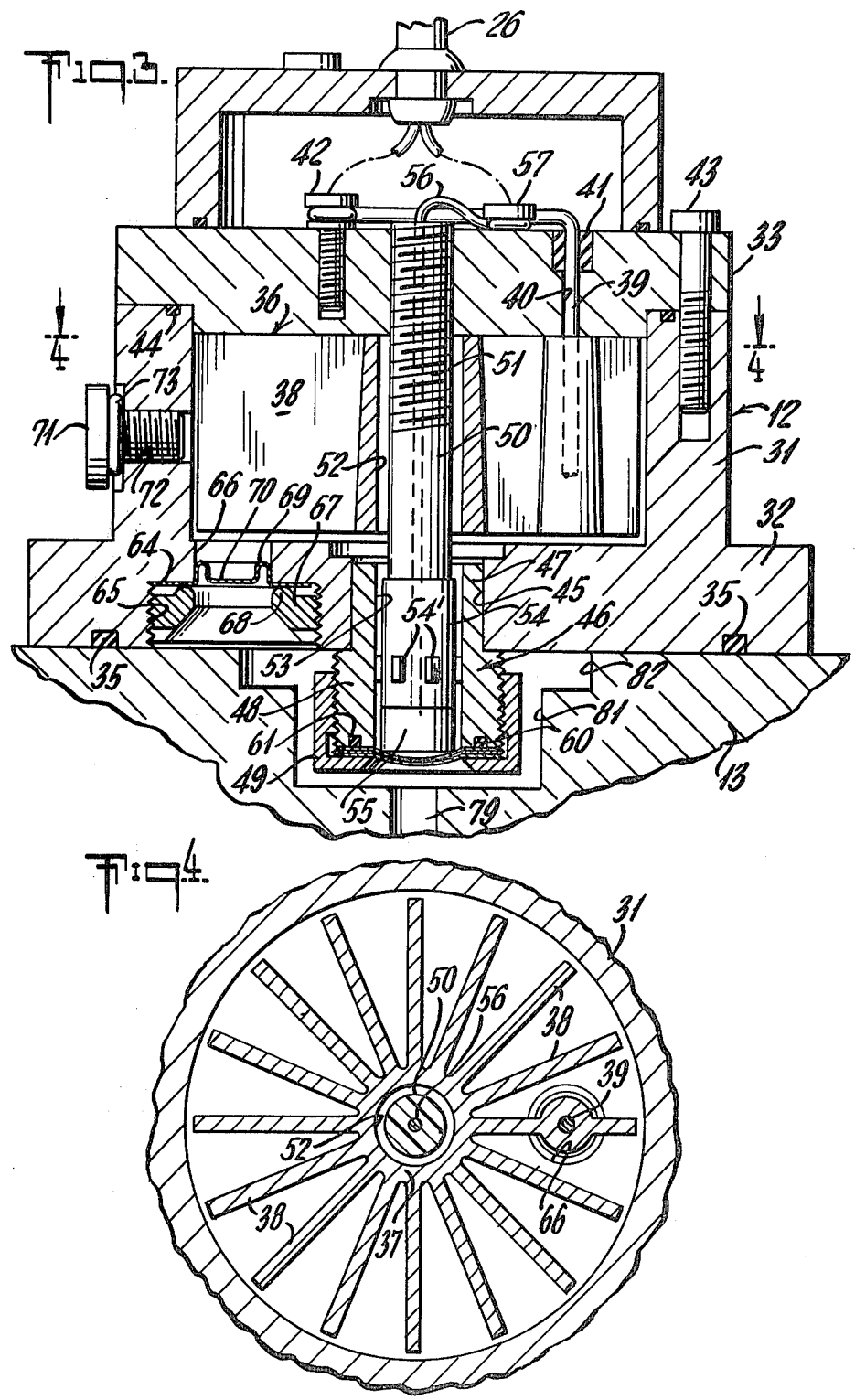

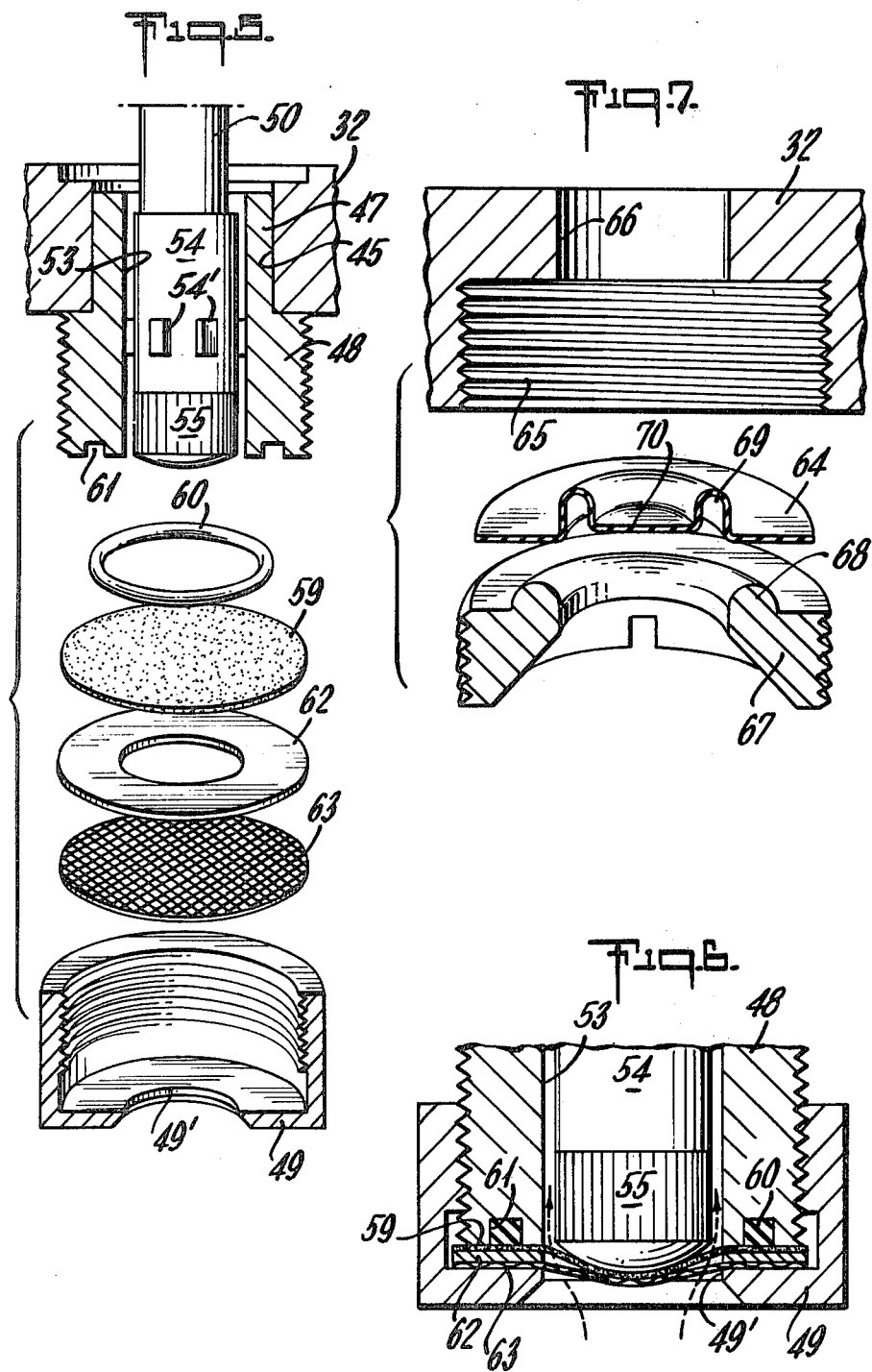

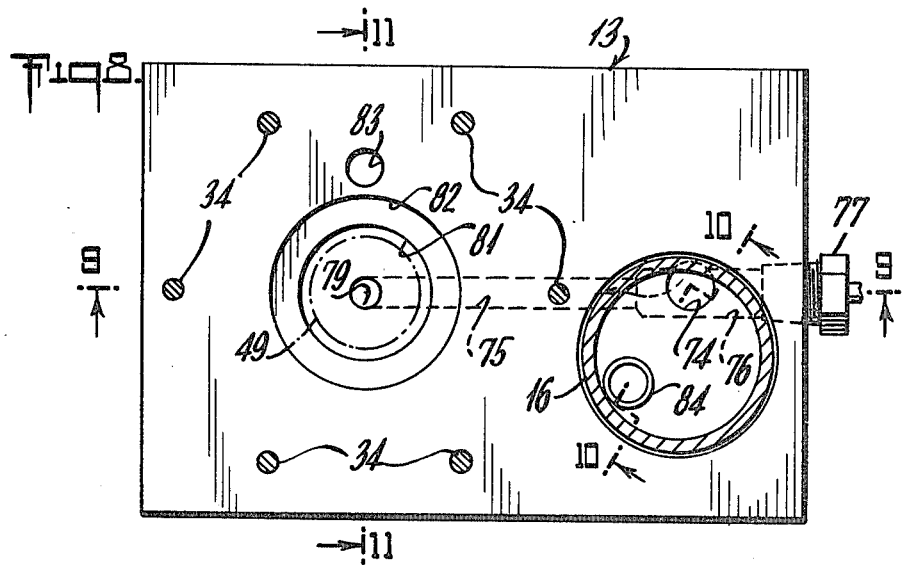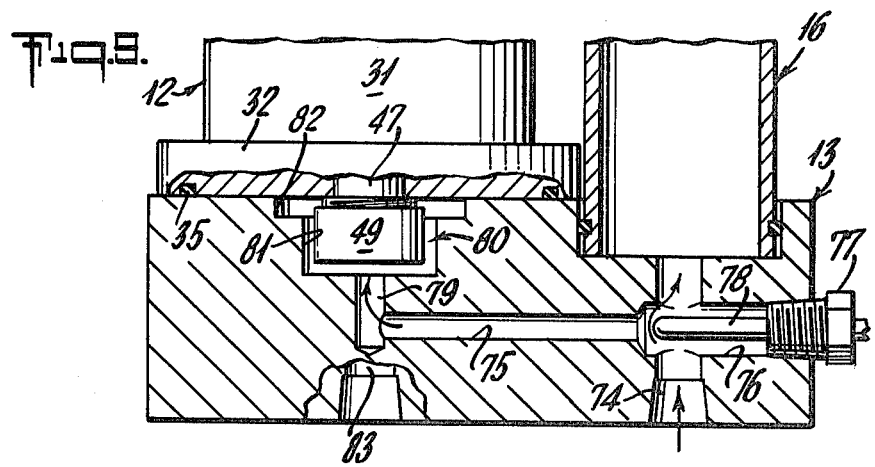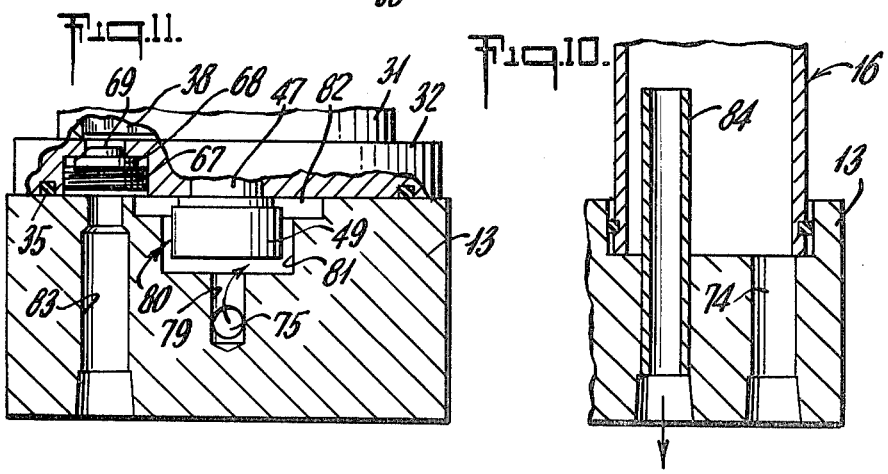

DISSOLVED OXYGEN ANALYZER

This invention relates to a dissolved oxygen analyzer and more specifically to a novel and improved oxygen sensor having a substantially linear response and particularly useful for the measurement of dissolved oxygen in boiler feed water. This improved sensor is capable of measuring the dissolved oxygen in water from 1 ppb. to substantially saturated water having approximately 8400 ppb.

Dissolved oxygen analyzers are particularly important in connection with the operation of boiler plants utilizing high temperature and high pressure steam. Under such conditions even small quantitites of dissolved oxygen in the water react readily with the iron to form soft iron oxides which readily flake off of the metal surfaces and produce a sludge which must be periodically removed. The pitting of both the boiler as well as associated piping can eventually erode the metals sufficiently to cause serious breakdowns and of course interruption of the operation of the plant. Dissolved oxygen also facilitates electrolytic action between dissimilar metals which results in corrosion and leakage at the joints. Therefore, to minimize oxidation and corrosive effects of dissolved oxygen, mechanical deaerators and chemical additives are utilized to remove the oxygen. However, it is essential that a constant check be maintained on the dissolved oxygen to be certain that it is maintained at a very low level. In this way, the quantity of chemical additives can be controlled to maintain the oxygen at the desirable low level and avoid the excessive use of additives which has also been found to be harmful.

While dissolved oxygen analyzers have been used for many years for the measurement of dissolved oxygen in boiler feed water, known analyzers have often been found to behave erratically, require substantial time for stabilization when placed into use and require frequent maintenance. Moreover, many known prior art devices generally required removal of gas from the water being tested and the utilization of chemical additives.

This invention overcomes the difficulties heretofore encountered in the measurement of dissolved oxygen and provides a novel and improved sensor which can be placed in a continuous flowing sample of the boiler feed water without any preconditioning of the feed water whatsoever. Moreover, the sensor is extremely stable and affords a rapid response and a continuous output signal. It has also been found that under conditions equivalent to normal power plant operation that maintenance would only be required every three to twelve months and the maintenance would merely require ten to fifteen minutes. Under these conditions operation of the boiler plant need not be interrupted.

Another object of the invention resides in the provision of a novel and improved dissolved oxygen analyzer which is characterized by its simplicity, stability and reliability of measurement of 1 ppb. of dissolved oxygen to approximately 8400 ppb. of dissolved oxygen which is generally equivalent to saturation.

Still another object of the invention resides in the provision of a novel and improved oxygen analyzer which can be quickly and easily calibrated while in its normal operating position and with the calibrating procedure requiring not more than five minutes. In the event the calibration procedure should indicate the need for maintenance, the maintenance procedure would not require more than ten to fifteen minutes. Under these conditions calibration and maintenance can be effected without interrupting the operation of the boiler plant or endangering it in any way.

The dissolved oxygen sensor in accordance with the invention involves the utilization of a relatively large electrode formed of lead and a second electrode formed of silver. The silver electrode protrudes slightly from the cell itself and is enclosed by an oxygen permeable membrane. The sample feed water is then permitted to flow by the membrane so that oxygen in the boiler feed water will defuse through the membrane where it is reduced at the silver cathode immediately behind the membrane. The resultant cell reactions are as follows:

at the cathode:

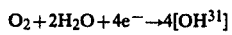

at the anode:

Means are also provided to equalize the pressure of the electrolyte within the cell with the pressure of the boiler feed water sample being tested. As will be shown means are provided to insure a substantially constant pressure and flow of the sample water being tested.

The above and other objects and advantages of the invention will become more apparent from the following description and accompanying drawings forming part of this application.

IN THE DRAWINGS

FIG. 1 is a front elevational view of apparatus embodying the novel and improved dissolved oxygen sensor in accordance with the invention for measuring dissolved oxygen in a boiler feed water sample, FIG. 2 is a side elevational view of the apparatus illustrated in FIG. 1, FIG. 3 is a cross sectional view of the novel and improved dissolved oxygen sensor in accordance with the invention, FIG. 4 is a cross sectional view of FIG. 3 taken along the line 4—4 thereof, FIG. 5 is an exploded perspective view of the silver electrode and the positioning of the oxygen permeable membrane assembly enclosing the electrode and sealing the cell, FIG. 6 is a cross sectional view of the elements shown in FIG. 5 in their assembled positions, FIG. 7 is an exploded cross sectional view of the pressure compensating means forming part of the sensor, FIG. 8 is a plan view of the detector mount and sample water supplying means taken along the line 8—8 of FIG. 1, FIG. 9 is a cross sectional view of FIG. 8 taken along the line 9—9 thereof, FIG. 10 is a cross sectional view of FIG. 8 taken along the line 10—10 thereof, and FIG. 11 is a cross sectional view of FIG. 8 taken along the line 11—11 thereof.

Referring now to the drawings and more specifically to FIGS. 1 and 2, the oxygen analyzer is contained within a housing 10 normally closed by a cover 11. The dissolved oxygen sensor in accordance with the invention is denoted by the numeral 12 and is carried by a base 13 having a sample water inlet pipe 14, a discharge pipe 15 and a contant head chamber 16 to provide both a constant flow and pressure of the sample water being tested. Feed water sample line 17 enters the bottom of the housing and is coupled through a control valve 18 to the water line 14 through a T-connector 19. A valve 20 having a water inlet 21 is coupled to the side opening 22 of the T-connector. The inlet 21 is utilized for feeding water having a known quantity of dissolved oxygen through the detector for purposes of calibration. In calibrating the detector, the valve 18 may be closed while the valve 20 would be opened and saturated water passed through opening 21. In the alternative, a known current may be applied through leads 90' to a conventional Faraday cell 90 having electrodes projecting into water sample flowing through inlet 17. With either method a known concentration of dissolved oxygen is produced and can be utilized to check the calibration on the dissolved oxygen sensor 12 without removing it from its position in the apparatus. Water discharged through the outlet 15 and from a second outlet 23 from the constant head chamber 16 flows into the tank 24 whereupon it is discharged through the discharge pipe 25.

The electrical signal produced by the cell 12 is fed through leads 26 and cable 27 to an amplifier 28 and indicator 29. At the same time the thermistor 30 which as will be shown is positioned in the incoming sample water measures the temperature of the water and the thermistor is connected through the leads 30' and cable 27 to compensate automatically the operation of the amplifier for changes in the temperature of the boiler feed water sample.

FIGS. 3 through 7 illustrate one embodiment of a novel and improved dissolved oxygen sensor 12 in accordance with the invention. The sensor 12 includes an annular body 31 having a peripheral outwardly extending flange portion 32 and a cover 33 overlying the body portion 31. The sensor is fastened in place on the base 13 by a plurality of bolts 34, illustrated in FIG. 1, and is sealed to the base by an O-ring 35. A lead anode 36 is disposed within the housing 31 and has a hollow central core 37 with a plurality of outwardly extending ribs or fins 38. For convenience, the anode may either be made in one piece or in sections electrically coupled one to the other by lead solder. Both the lead solder and the lead anode should be substantially pure lead preferably having a purity of 99% or better. The anode is connected by a pure lead wire 39 which extends upwardly through an opening 40 in the cover 33 and through a gasket 41 to terminal 42 threadably engaging the cover 33. The housing 31 and the cover 33 should preferably be formed of a non-hydroscopic insulating material and preferably calendered polyvinylchloride or a molded expoxy resin. The cover 33 is secured to the housing 31 by a plurality of bolts 43 and is sealed by an O-ring 44.

The bottom of the housing 31 has an opening 45 for receiving an annular coupling member 46 which includes a shank portion 47 adhesively secured within the opening 45 and can outwardly extend the threaded portion 48 to receive a threaded cap 49 of metal or other suitable material. A centrally disposed cathode support 50 has a threaded portion 51 threadably engaging a cooperating opening in the cover 33. It extends downwardly through the central opening 52 in the anode and the central opening 53 in the coupling member 46. The lower portion 54 of the central member 50 is slightly larger in diameter than the remainder of the central member but is smaller in diameter than the opening 53 and has a plurality of projections 54 to center it within the opening 53. The lower end of the member 50 carries a cap 55 formed of pure silver having a purity of at least 99% which forms the cathode. A silver conductor 56 is soldered to the cathode 53 utilizing silver of equal purity or otherwise attached thereto to form a positive silver to silver contact. The conductor 56 extends through a central opening in the central member 50 and is fastened to the terminal 57 carried by the cover 33.

The silver electrode 55 is enclosed by an oxygen permeable membrane 59 having a low temperature coefficient and preferably formed of a silicone polycarbonate copolymer having a thickness of approximately 2 mils. The membrane 59 overlies the silver electrode and is sealed thereto by an O-ring 60 lying within the groove 61 on the threaded member 48 surrounding the electrode 55. A washer 62 overlies the membrane 59 and a screen 63 preferably formed of polyethylene and having a thickness of approximately 8 mils overlies the washer 62. The assembly, as will be observed in FIG. 5, is then held in place by a cap 49 having a central opening 49'. As will be shown, the sample water being tested flows around the cap 49 and oxygen will fliter through the membrane 59 and be reduced at the silver cathode.

In order to equalize pressure within the cell 12 with the pressure of the water sample being tested, an impervious flexible pressure membrane 64 is utilized. This membrane is disposed within a threaded opening 65 formed in the flange 32 of the cell. The opening 65 communicates with the interior of the cell by means of the passage 66 and the membrane is held in place by an externally threaded annular plug 67 having an annular ridge 68 with a curved upper surface which bears against the membrane 64 and thereby seals the passage 66. The central portion of the membrane 64 has an annular recess 69 formed therein which provides a central portion 70 that will deflect readily to compensate for pressure difference. The body 31 of the cell 12 also includes a plastic plug 71 as shown in FIG. 3 which threadably engages an opening 72 for the purpose of filling the cell with an electrolyte. The plug 71 is sealed to the housing 31 by a suitable O-ring 73.

The base 13 carrying the cell 12 is shown more clearly in FIGS. 8 through 11. Sample feed water flowing through the inlet pipe 14 is fed into the opening 74 in the base 13 and then upwardly to a transverse opening or passage 75. An enlarged portion 76 of the passage 75 opens into one side of the base 13 and this opening threadably receives a plug 77 carrying a thermistor 78 on the inner end thereof. Lead wires from this thermistor are interconnected with the amplifier as described in connection with FIG. 1. The sample water flowing through the passage 75 enters a vertical passage 79 and then flows into a well 80 having a lower portion 81 adapted to receive the cap 49 surrounding the silver electrode 55. The upper portion 82 of the well 80 is of enlarged diameter and enables the sample water to communicate with the pressure equalizing means as shown in FIGS. 3 and 9. The sample water is then discharged through a passage 83 and an outlet pipe 15 coupled thereto as shown in FIG. 1.

In order to maintain uniform pressure of the water being sampled, the incoming water supply is fed from the passage 76 into the constant head chamber 16. An overflow pipe 84 extends into the chamber 16 and this pipe is coupled to the discharge pipe 23 as described in FIG. 1. With this arrangement, the sample water pressure is maintained substantially constant at all times. At the same time the pressure within the cell 12 is automatically equalized with the pressure of the sample water.

With the cell as described above, it has been found that conditions of reversed polarity are not experienced and the electrical output from the cell at all times bears a substantially linear and uniform relationship with the quantity of dissolved oxygen in the sample water. Prior known cells have often produced a reversed polarity which functioned essentially as a negative bias and thus resulted in highly inaccurate readings of the quantity of dissolved oxygen. With the sensor in accordance with the invention and with the sample water being at 20° C. at sea level, it will develop an output of 0.007 microamperes for 1 ppb of dissolved oxygen. The output is substantially linear throughout the entire range from 1 ppb to saturated water which has approximately 8400 ppb of dissolved oxygen.

A preferred electrolyte for use in the sensor 12 includes 220 grams of potassium bicarbonate, 70 grams of sodium carbonate and 2 liters of distilled water. It is also desirable to depress the pressure membrane 64 slightly when filling the cell with the electrolyte so that the cell will be under a slight vacuum just prior to installation on the base 13.

As pointed out above, maintenance of the sensor in accordance with the invention is essentially limited to replacement of the membrane 59. This can be readily accomplished by removing the screws 34, attaching the sensor 12 to the base 13, removing the cap 49 for replacement of the membrane and then refilling the cell with electrolyte if needed. This entire operation requires of the order of 10 to 15 minutes and the membrane life in normal power operation is from 3 to 12 months. Checking the accuracy of the sensor can be quickly effected by merely applying a current to the Faraday cell 90 to produce a known concentration of oxygen in the sample water flowing through the inlet pipe 14. Since this takes but a few minutes, the test can be effected periodically without interfering with the operation of the boiler plant and readings from the sensor 12 are substantially instantaneous.

While only one embodiment of the invention has been illustrated and described, it is understood that alterations, changes and modifications may be made without departing from the true scope and spirit thereof.

What is claimed is:

1. An oxygen sensor for measuring dissolved oxygen in water, comprising a hollow housing of non-hydroscopic calendared polyvinylchloride or molded epoxy resin having a liquid filler plug in one housing wall, said housing including an opening closed by an oxygen permeable membrane, a substantially pure lead anode electrode within said housing and a conductor of substantially pure lead connected to said anode and extending through the housing wall, a substantially pure silver cathode within said housing and positioned in close proximity to said membrane, a conductor of substantially pure silver connected to said cathode and extending through said housing wall, and an electrolyte filling said housing, whereby dissolved oxygen in water circulated about the outer side of said membrane will penetrate said membrane and produce a current through indicating means connected to said conductors which is proportional to the quantity of dissolved oxygen in said water.

2. An oxygen sensor according to claim 1 wherein the purity of said anode, cathode and the anode and cathode conductors is approximately 99%.

3. An oxygen sensor according to claim 1 wherein said membrane is a silicone polycarbonate copolymer.

4. An oxygen sensor according to claim 1 including indicating means coupled to said conductors and means for sensing the temperature of said water and connected to said indicating means to modify the operation of said indicating means in accordance with changes in temperature of said water.

5. An oxygen sensor according to claim 1 wherein said anode has a hollow cylindrical member extending therethrough and fins extending outwardly therefrom, said opening is aligned with said cylindrical member, said cathode is carried by a central member extending through said cylindrical member with said conductor extending through said central member.

6. An oxygen sensor according to claim 5 wherein said housing includes a second opening and a flexible impervious diaphragm closing said opening whereby said water upon being circulated about said diaphragm will equalize the pressure of the electrolyte within the housing with the pressure of said water.

7. An oxygen sensor according to claim 6 wherein said housing has a bottom wall including said openings closed by said membrane and said diaphragm and said analyzer further includes a base having a recess therein, means securing said sensor to said base with said openings in communication with said recess, a first passage within said base communicating with said recess, means for feeding water to be tested to said passage, and a second water discharge passage within said base and communicating with said recess.

8. An oxygen sensor according to claim 7 wherein said base further includes a constant head chamber, a passage communicating with said first passage and said chamber and a discharge conduit extending into said chamber to maintain a predetermined liquid level therein.

* * * * *